United States Patent
Hill et al.

(10) Patent No.: US 9,629,572 B2
(45) Date of Patent: Apr. 25, 2017

(54) SLEEP DISORDER DIAGNOSTIC SYSTEM AND METHOD

(75) Inventors: Phoebe Katherine Hill, Roseville (AU); Mark Bertinetti, Lane Cove (AU); Rohan Neil Primrose, Marsfield (AU); Gregory Robert Peake, Kingsford (AU); Philip Rodney Kwok, Chatswood (AU)

(73) Assignee: ResMed Limited, Bella Vista (AU)

( * ) Notice: Subject to any disclaimer, the term of this patent is extended or adjusted under 35 U.S.C. 154(b) by 3346 days.

(21) Appl. No.: 11/509,093

(22) Filed: Aug. 24, 2006

(65) Prior Publication Data
US 2007/0049842 A1    Mar. 1, 2007

(30) Foreign Application Priority Data

Aug. 26, 2005 (AU) ................................ 2005904652
Nov. 10, 2005 (AU) ................................ 2005906244

(51) Int. Cl.
*A61B 5/02* (2006.01)
*A61B 5/08* (2006.01)
*A61B 5/00* (2006.01)
*A61B 5/0476* (2006.01)

(52) U.S. Cl.
CPC .............. *A61B 5/08* (2013.01); *A61B 5/4806* (2013.01); *A61B 5/4818* (2013.01); *A61B 5/6804* (2013.01); *A61B 5/6887* (2013.01); *A61B 5/0002* (2013.01); *A61B 5/0476* (2013.01)

(58) Field of Classification Search
CPC .... A61B 5/6884; A61B 5/4818; A61B 5/4806
USPC ................................ 600/300, 483, 529, 552
See application file for complete search history.

(56) References Cited

U.S. PATENT DOCUMENTS

| | | | | |
|---|---|---|---|---|
| 5,551,423 A | * | 9/1996 | Sugiura | ......................... 600/323 |
| 5,937,853 A | * | 8/1999 | Strom | ...................... 128/204.23 |
| 6,687,523 B1 | * | 2/2004 | Jayaramen et al. | .......... 600/388 |
| 6,705,315 B2 | | 3/2004 | Sullivan et al. | |

(Continued)

FOREIGN PATENT DOCUMENTS

| | | |
|---|---|---|
| WO | WO 02/02169 | 1/2002 |
| WO | WO 02/18002 | 3/2002 |

(Continued)

OTHER PUBLICATIONS

U.S. Appl. No. 60/505,718, filed Sep. 2003, Kwok.

*Primary Examiner* — Christian Jang
(74) *Attorney, Agent, or Firm* — Nixon & Vanderhye PC

(57) ABSTRACT

Systems and/or methods for diagnosing sleep disorders in a patient are provided. In certain example embodiments, articles of bed clothing and/or bed sheets comprising sensors operable to obtain patient condition data related to sleep-disordered breathing (SDB) are provided to patients. The patient condition data is stored to a data recorder operably connected to the sensors. The sensors and the data recorder may communicate wirelessly. The bed clothing (e.g. wearable articles of clothing, bed sheets or mats, pillows, etc.) may have batteries and/or battery fibers disposed therein to power the sensors. In certain example embodiments, a bed sheet may be physically connected to a power supply and/or the data recorder. In certain example embodiments, a bed sheet and articles of bed clothing both may be provided to the patient.

43 Claims, 11 Drawing Sheets

(56) References Cited

U.S. PATENT DOCUMENTS

| | | | |
|---|---|---|---|
| 7,277,749 B2* | 10/2007 | Gordon et al. | 607/2 |
| 7,334,280 B1* | 2/2008 | Swartzburg | A47C 21/046 5/652.1 |
| 7,497,838 B1* | 3/2009 | Dunagan | A61F 13/046 602/13 |
| 2001/0044573 A1* | 11/2001 | Manoli et al. | 600/383 |
| 2001/0047992 A1* | 12/2001 | Deangelis et al. | 219/529 |
| 2002/0019586 A1* | 2/2002 | Teller | A61B 5/02055 600/300 |
| 2002/0028988 A1* | 3/2002 | Suzuki et al. | 600/300 |
| 2002/0032386 A1* | 3/2002 | Sackner et al. | 600/536 |
| 2002/0151772 A1* | 10/2002 | Polak | 600/310 |
| 2002/0165462 A1* | 11/2002 | Westbrook et al. | 600/529 |
| 2002/0198443 A1* | 12/2002 | Ting | 600/323 |
| 2003/0024343 A1* | 2/2003 | Perezlmize | B62D 1/06 74/558 |
| 2003/0066529 A1 | 4/2003 | Truschel et al. | |
| 2004/0007695 A1* | 1/2004 | Anquetil et al. | 252/500 |
| 2004/0048038 A1* | 3/2004 | Tseng | B32B 27/00 428/131 |
| 2004/0097823 A1* | 5/2004 | Friedrichs et al. | 600/534 |
| 2005/0245839 A1* | 11/2005 | Stivoric | G06F 19/3418 600/549 |
| 2006/0183980 A1* | 8/2006 | Yang | 600/301 |
| 2007/0093722 A1* | 4/2007 | Noda et al. | 600/533 |

FOREIGN PATENT DOCUMENTS

| | | |
|---|---|---|
| WO | WO 03/024335 | 3/2003 |
| WO | WO 2005/028009 | 3/2005 |
| WO | WO 2005/099798 | 10/2005 |

* cited by examiner

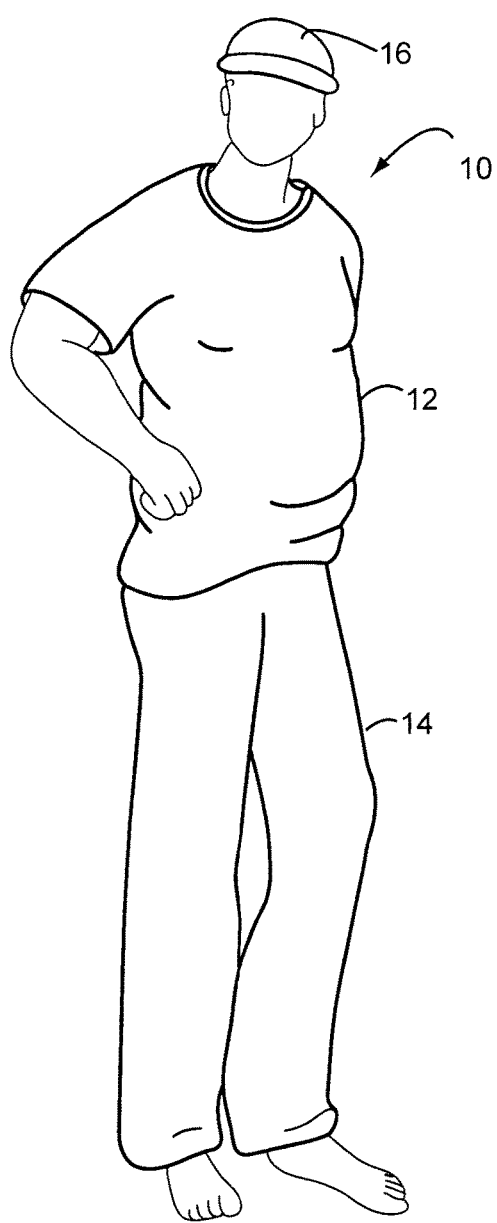 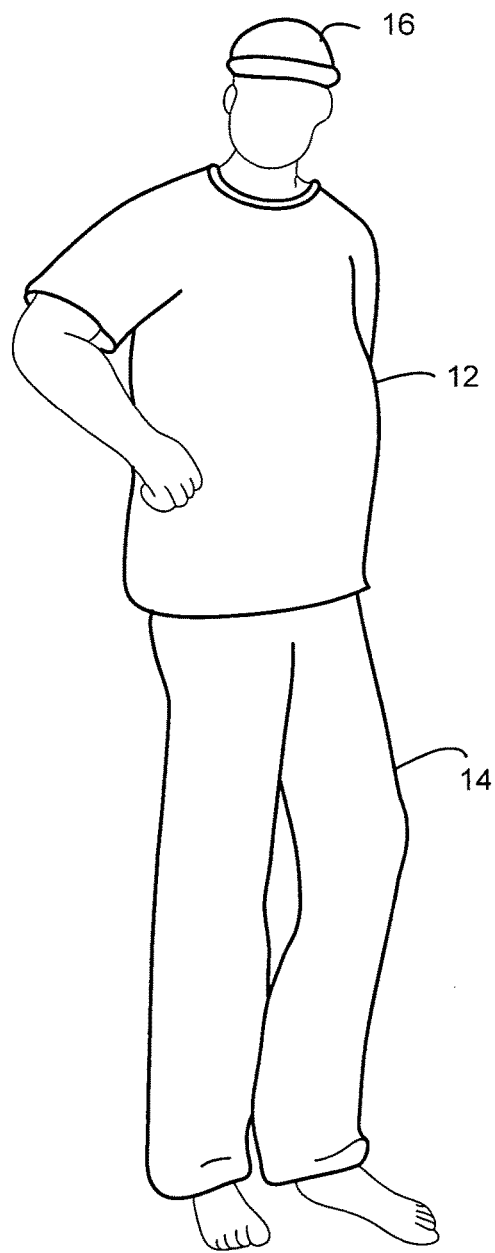
FIG. 1a          FIG. 1b

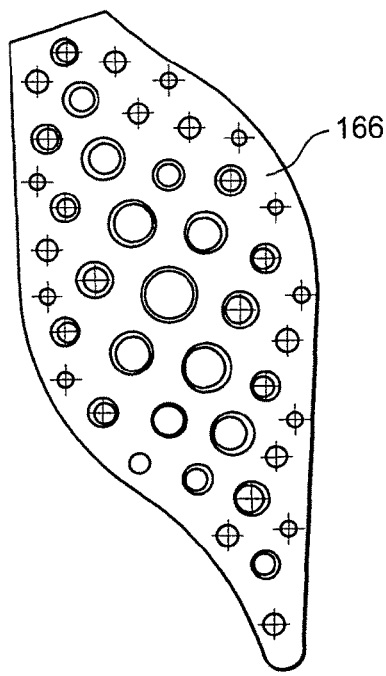
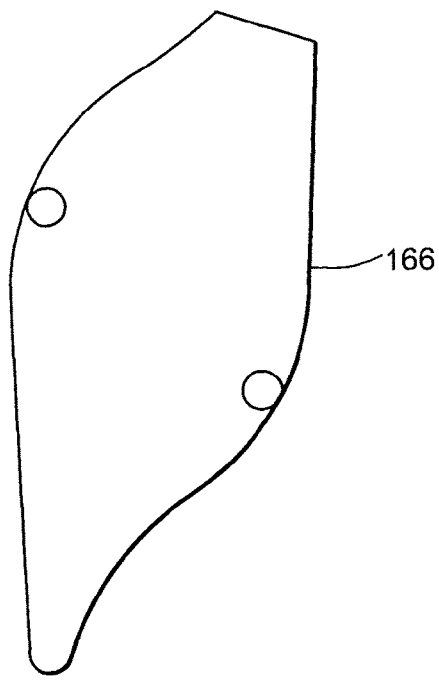
FIG. 8a
FIG. 8b
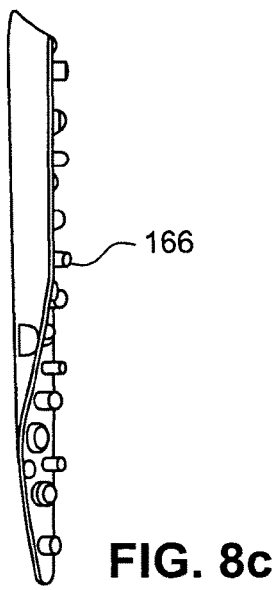
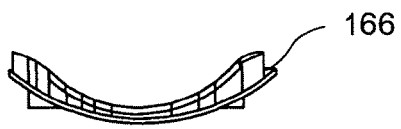
FIG. 8d
FIG. 8c
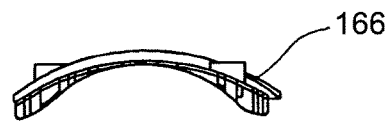
FIG. 8e

SLEEP DISORDER DIAGNOSTIC SYSTEM AND METHOD

CROSS-REFERENCE TO PRIORITY APPLICATIONS

This application claims the benefit of Australian Provisional Application No. 2005904652, filed 26 Aug. 2005, and Australian Provisional Application No. 2005906244, filed 10 Nov. 2005, each expressly incorporated by cross-reference in its entirety.

FIELD OF THE INVENTION

The example embodiments herein relate to an apparatus and/or method for diagnosing sleep disorders in a patient. More particularly, the example embodiments herein relate to bed clothing (e.g. wearable articles of clothing, bed sheets or mats, pillows, etc.) comprising sensors operable to obtain patient condition data related to sleep-disordered breathing (SDB) and data recorders in operable communication with the sensors. The wearable clothing and/or bed sheets may have batteries and/or conductive fibers woven therein to power the sensors.

BACKGROUND OF THE INVENTION

Sleep disorders are considered a large but under-diagnosed problem in society today. There are over seventy different sleep disorders that are believed to contribute to a range of health and social problems. Insufficient quality sleep is thought to be a contributing factor in many work- and car-related accidents and to many common health problems such as hypertension, depression, cardiovascular disease, diabetes, and kidney disease. Thus, sleep disorders are thought to have a significant health and economic impact on society.

The most common disorder is Obstructive Sleep Apnea (OSA) Syndrome. OSA is a sleep and breathing disorder where the upper airway partially or completely occludes during sleep. The presence of OSA Syndrome is defined as at least five obstructed breathing episodes per hour of sleep together with daytime sleepiness symptoms. Some studies estimate that OSA Syndrome affects approximately 2-4% of the general population. There are a number of factors that increase the risk of OSA Syndrome including age, sex, and weight. The prevalence in males and females over 30 years of age may be closer to 24% and 9% respectively. Thus, this disorder has a significant impact on society. However, the diagnosis and treatment rates for this disorder currently are very low.

Excess tissue in the upper airway and physical abnormalities worsen OSA. During sleep, especially in REM sleep, our bodies relax, and muscle tissues like the tongue and soft palate lose their slight rigidity, and the airway collapses. When these tissues obstruct the upper airway completely, they prevent breathing and can actually begin to suffocate the sleeper. The sleeper wakes up enough to regain control of the upper airway, breathes again, and then falls back to sleep. This happens from dozens to hundreds of times per night for people with OSA, but they usually do not remember waking up.

Each obstruction deprives the body of oxygen and does not allow it to get rid of carbon dioxide that it would normally exhale. When the body sets off "alarms" that it needs more oxygen, the brain wakes the sleeper, breathing resumes, and the individual falls back asleep until the next obstruction occurs. These obstructions increase heart rate, raise blood pressure, and eventually blunt the body's automatic response system, allowing increasingly more severe apneas and hypopneas.

OSA may have a significant impact on an individual's health. Because of the disruption in sleep, a common symptom of OSA is daytime sleepiness. Daytime sleepiness may impact an individual's performance and/or ability to control machinery. For example daytime sleepiness caused by OSA may impair an individual's ability to drive a car and may be a factor in car accidents.

The current method of treatment for OSA is positive airway pressure (PAP) delivered to an individual's airways while they are asleep. Colin Sullivan was the first to invent the use of nasal Continuous Positive Airway Pressure (CPAP) to treat Obstructive Sleep Apnea (OSA). See U.S. Pat. No. 4,944,310. The treatment generally provides a continuous supply of air or breathable gas from a blower or flow generator to a patient via an air delivery conduit and a patient interface, such as a full-face or nasal mask or nasal prongs. The air or breathable gas is commonly delivered at a pressure of 4-20 $cmH_2O$ and acts as a splint to hold the airway open during sleep Further developments of CPAP have provided automatically adjusting devices that a patient could take home. The automatically adjusting device will raise and/or lower the treatment pressure based on indications of OSA, such as snoring. Such CPAP devices sometimes generically are referred to as Automatic Positive Airway Pressure (APAP) devices. An example of an APAP device is the ResMed Autoset® Spirit™. See U.S. Pat. Nos. 5,245,995; 6,398,739; and 6,635,021.

Another type of nasal CPAP device provides a first pressure during inhalation (typically termed IPAP) and a second, lower pressure during exhalation (typically termed EPAP). Examples of these include the ResMed VPAP™ series, and the Respironics BiPAP series. Bilevel CPAP devices may be prescribed for patients who do not comply with single pressure CPAP devices. Some patients perceive that the lower pressure during exhalation is more comfortable, at least while they are awake.

The current diagnosis and treatment process for OSA generally begins when an individual or their bed partner complains of daytime sleepiness or excess snoring. In this scenario, the individual would visit a GP for a referral to a sleep specialist. The individual would then make an appointment to visit the sleep specialist who would review the patient's symptoms and refer them to a sleep laboratory for diagnosis by polysomnography (PSG). For diagnosis and a treatment plan to be established, an individual generally needs to spend two nights in the sleep laboratory, with the first night being for diagnosis and the second night being for therapy titration.

Therapy titration identifies the correct treatment pressure required by the individual to overcome OSA, such that apneas are eliminated. The treatment pressure is usually in the range of 4-20 $cmH_2O$. Following diagnosis and therapy titration, an individual may purchase an appropriate therapy device that is set to the identified treatment pressure.

Unfortunately, this process is time consuming and expensive. There are often extensive waiting periods, from four weeks to two years or more, for a PSG at a sleep laboratory, with each PSG study costing in excess of $750. Also, the system relies on the individuals recognizing the symptoms and seeking medical advice. Currently, the awareness level of this disorder is low, which impacts the recognition of symptoms, diagnosis, and ultimately treatment.

There are also a number of portable Diagnostic Systems (PDS) currently available, such as the FLAGA Embletta® and the ApneaLink™ devices. These devices comprise data recorder units that generally are strapped around the patients' torso. A range of sensor components are connected to the data recorder units to deliver information relating to a range of sleep parameters, such as the pressure, air flow, oxygen saturation level, position, and sleep stage. However, these systems are uncomfortable for the wearer for a number of reasons. For example, the wires inhibit the wearers while they are trying to sleep, and the data recorder unit is relatively large and bulky, also inhibiting the wearers while the wearers are trying to sleep. Because of this discomfort, the results obtained by the systems sometimes are considered to be unreliable, as they do not accurately record a typical night's sleep for the patient.

More recently, there have been monitoring and sensing shirts designed that have sensors incorporated within their fibers, such as the Vivometrics® LifeShirt® (http://www.vivometrics.com) and the SensaTex™ SmartShirt (http://www.sensatex.com). The LifeShirt® eliminates many of the wires, but not the data recorder unit. The SensaTex™ SmartShirt attempts to eliminate both the wires and the data recorder through integrated electronic textile solutions.

The patents mentioned herein are hereby incorporated herein by reference in their entireties.

SUMMARY OF THE INVENTION

One aspect is to provide a diagnostic system for use in diagnosing a patient with a sleep disorder. Such systems may comprise at least one item of bed clothing, with the at least one item of bed clothing comprising at least one sensor. A data recorder may be in operable communication with the at least one sensor. A power source may be operable to supply power to the at least one sensor. The at least one sensor may be operable to monitor at least one sleeping disorder related parameter and further operable communicate the at least one sleeping disorder related parameter to the data recorder.

Certain other example embodiments relate to a method for diagnosing a patient with a sleep disorder. According to such example embodiments, at least one item of bed clothing may be provided to the patient, with the at least one item of bed clothing comprising at least one sensor. A signal corresponding to at least one sleeping disorder related parameter of the patient may be generated via the at least one sensor. The signal may be recorded onto a data recorder.

According to certain other example embodiments, a system for diagnosing a patient with a sleep disorder. Such systems may comprise at least one item of bed clothing for the patient, with the at least one item of bed clothing comprising at least one sensor. Means for generating a signal corresponding to at least one sleeping disorder related parameter of the patient may be included. Means for recording the signal onto a data recorder also may be included.

Another aspect of the invention relates to pajamas constructed from at least one piece of material, wherein the material includes at least one respiratory sensor woven or embedded therein.

Another aspect relates to a recording device shaped to be comfortably positioned on a patient, which includes a connector or receiver adapted to receive signals from at least one respiratory sensor. In one form, the recording device includes a wireless transmission unit adapted to send a signal to another device. In one form, the recording device includes a wireless transmission unit adapted to receive a signal from another device. In one form, the recording device includes a pad operable to space a main body of the recording device from the patient's body. In one form, the pad is constructed from Santoprene™.

In one form, the pajamas include a pocket configured to removably receive a recording device.

Another aspect relates to a data storage unit operable to receive and store a wireless respiratory signal from a recording device. In one form, the data storage unit includes a recharger to recharge a recording device. In one form, the data storage unit includes an indicator to display the status of at least one wireless respiratory signal. In one form, the data storage unit includes a start/stop button to activate at least one sensor in the pajamas.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 1a and 1b are perspective views of the diagnostic bed clothing including a shirt, pants, and a cap being worn by a patient according to an example embodiment;

FIG. 7b is a top view of a data storage case of FIG. 7a;

FIG. 7d is a front view of the data storage case of FIG. 7a;

FIGS. 8a, 8b, 8c, 8d and 8e show top, side, bottom, front, and back views, respectively, of a Santoprene molded portion that attaches to a data recorder according to an example embodiment;

DETAILED DESCRIPTION OF ILLUSTRATED EMBODIMENTS

1. Example Articles of Bed Clothing

Figure 2:
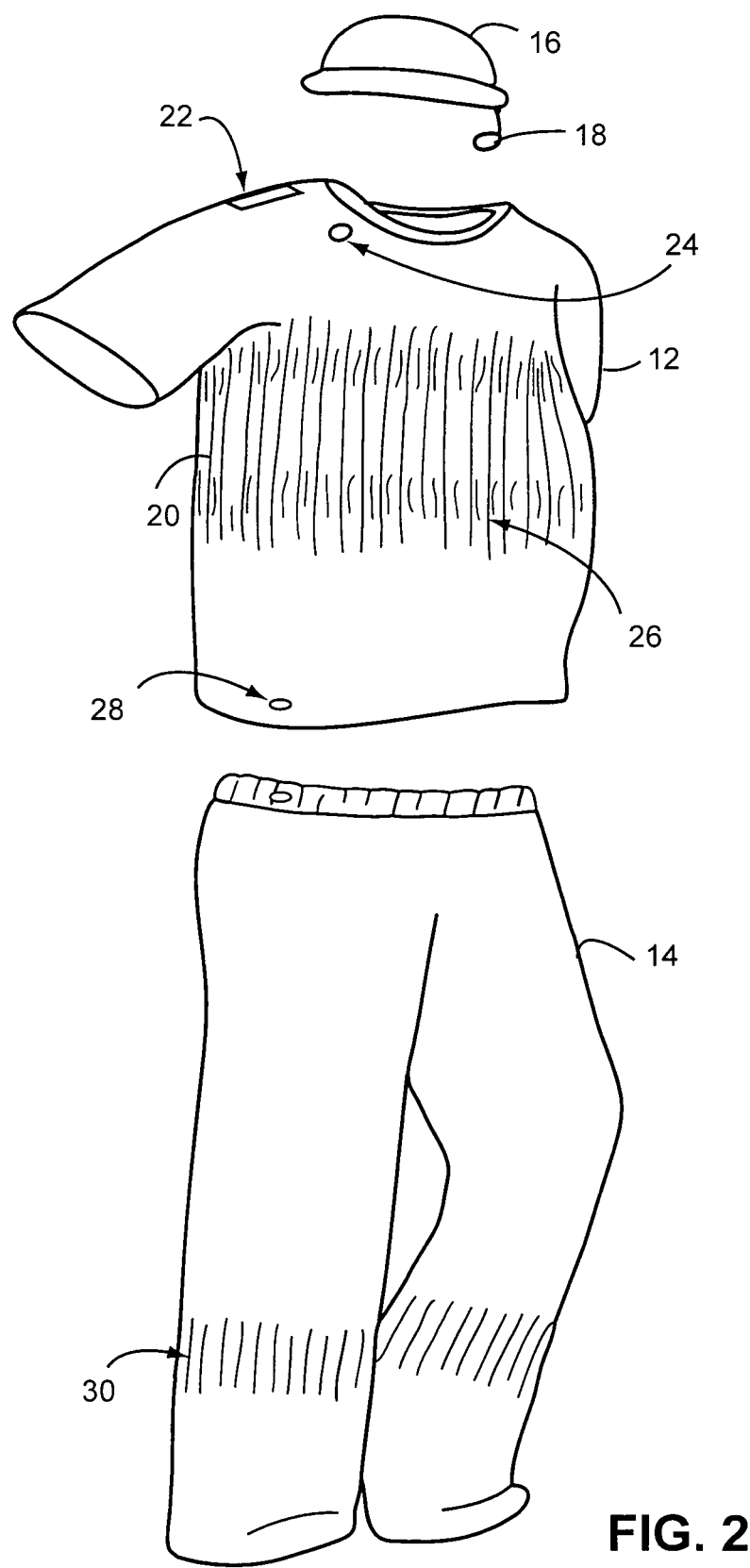
FIG. 2 is a perspective view of the diagnostic bed clothing of FIG. 1 showing the locations of sensors and electrodes according to an example embodiment.

FIGS. 1a, 1b, and 2 illustrate a diagnostic bed clothing apparatus 10 according to an example embodiment. The diagnostic bed clothing apparatus 10 may comprise, for example, a shirt 12, pants 14, and headgear 16. The shirt 12 may contract around the body of the patient for a close fit, as shown by FIGS. 1b and 2. The contraction of shirt 12 may be enabled by, for example, artificial muscle fibers 20. In certain example embodiments, the contracting of the shirt may be caused by a cinching mechanism (e.g. by pulling a cord), by Spandex™ or elastic, etc. Preferably, the system will be used while the patient is sleeping to gather information related to the patient's sleep, such as, for example, patient orientation, movement, heart rate, oxygen saturation, snore, the presence of an apnea and/or hypopnea, etc.

In certain example embodiments, the bed clothing may be made from a lightweight material such that a person may wear the bed clothing under their standard bed clothing. Optionally, the bed clothing may be made from a material adapted to draw moisture away from the patient's body to assist in keeping the person cool. As used herein, the term bed clothing or clothes includes, for example, wearable clothing (e.g. shirts, pants, caps, etc.) as well as other bedding (e.g. bed sheets, blankets, pads, pillows, etc.).

1.1 Example Embodiment 1—Shirt, Pants, and Optional Headgear

The diagnostic bed clothing may have a fully integrated diagnostic system incorporated into it including one or more sensors, for example, electrodes, respiratory effort sensors 26, body position sensors, and oximeter 18. A textile switch 24 may be used to activate the sensors. The system may send the information it gathers to a data recorder using wireless technology, such as, for example, Bluetooth technology, and the system may operate on a power source, e.g., a small battery 22, located in the shoulder of the garment (e.g. in a pocket formed therein) or any other appropriate location in the garment. While the power source in this example is a battery, it could also be a system that plugs into a wall socket. It will be appreciated that any type of wireless communication protocol may be implemented in certain example embodiments. The battery 22 may be removable to allow the washing of the shirt. In certain example embodiments, the battery 22 may be replaceable and/or rechargeable. A fastener 28 connects the shirt 12 and the pants 14, allowing data and/or power to flow between the articles.

In contrast to other monitoring shirts and in the interest of comfort, the shirt is loose fitting, at least initially. As noted above, the shirt may become fitted to record accurate data, for example, after the diagnostic system is activated. This may enable certain example embodiments to provide more accurate data collection and recording compared to loose-fitting conventional systems, for example, because the electrodes and sensors are located close to the skin after the shirt contracts and becomes fitted.

The pants of the bed clothing may contain movement sensor electrodes 30 to measure movement while the patient is being studied. According to an example embodiment, headgear 16, in the form of a cap or hat, optionally with EEG capabilities, also is available. The headgear 16 may comprise an EEG sensor, and may advantageously provide data to allow for a determination of the patient's stage of sleep. The headgear also may comprise an oximeter 18 that attaches to the earlobe. In certain other example embodiments, an oximeter may be attached to a patient's finger and operably connected to a data recorder located within or on the diagnostic bed clothing system (not shown). For example, the bed clothing may comprise a glove that includes an oximetry sensor at one of the fingertips.

1.2 Example Embodiment 2—Shirt and Pants

Figure 3A:
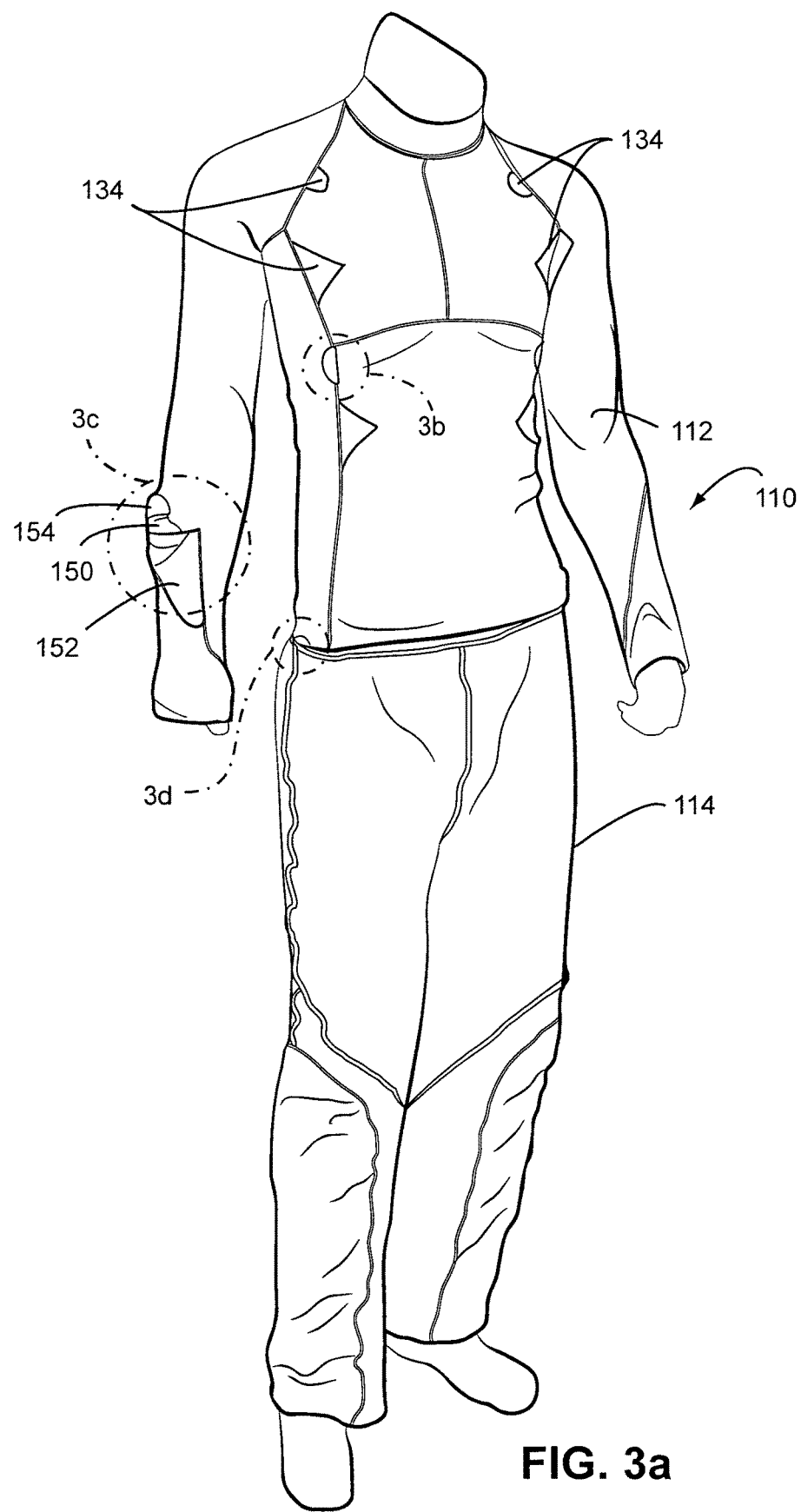
FIG. 3a is a more detailed view of an example embodiment of the diagnostic bed clothing.
Figure 3B:
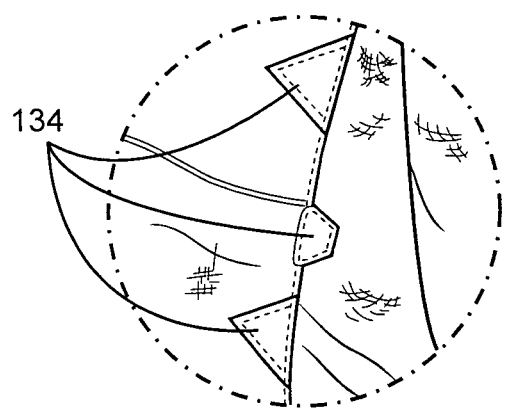
FIGS. 3b, 3c and 3d are enlarged sections of the diagnostic bed clothing of FIG. 3a, indicating sample locations of sensors, the sensor unit pocket, and power connection, respectively.
Figure 3C:
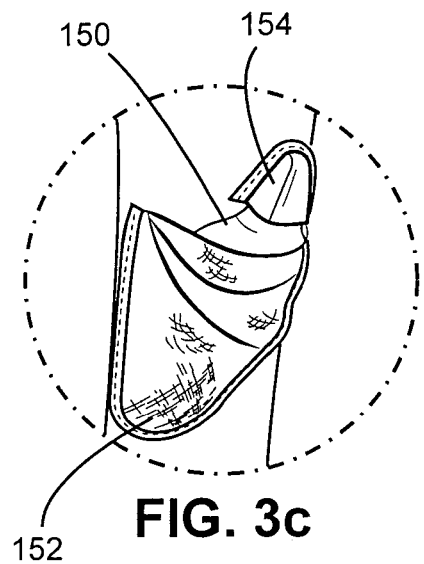

FIG. 3a shows another example embodiment of the diagnostic bed clothing apparatus 110. The diagnostic bed clothing 110 comprises a shirt 112 and pants or shorts 114. A conductive fiber wiring system, which may be woven into the fabric of diagnostic bed clothing 112, may be used to create the electrodes and the sensors 134 (described in more detail below), and to provide power to the diagnostic bed clothing apparatus 110. A data recorder 150 may be located in a pocket 152 on the sleeve of the shirt 112 (see FIG. 3c). Data recorder 150 may record, at least temporarily, information gathered from one or more sensors disposed within the bed clothing. It also may be used in connection with a data storage case (described in greater detail below) to transfer information to another device such as, for example, a computer, PDA, etc. The data recorder 150 may be removable to facilitate the laundering of the diagnostic bed clothing apparatus 110. A data connector 154 may be attached to the shirt 112 and is in operable connection with (e.g. plugs into) a first connection port 162 (see FIGS. 4, 6a and 6c) of the data recorder 150. The data connector 154 operably connects the sensors 134 to the data recorder 150, for example, via the conductive fiber wiring system. At the opposite end of the sensor device, wiring for an oximeter device (not shown) to be attached to the patient's finger in a conventional manner, and/or a nasal cannula (also not shown), may be connected to the data recorder 150 via an optional second connection port 164 (see FIGS. 4, 6a, and 6d). The sensors 134 may be located within the diagnostic bed clothing system (see FIG. 3b), and they may be positioned in a range of locations to enable a number of different parameters to be recorded. For example, in addition to, or in place of, the parameters that may monitored above described with reference to Example Embodiment 1 above, the sensors 134 may comprise, for example, ECG and EMG electrodes, orientation sensors, movement sensors, etc.

1.3 Example Throat Cuff

A further example embodiment of the bed clothing system may comprise a throat cuff. The throat cuff may sense vibrations in the throat to indicate snoring and/or muscle tone in the neck. These parameters may provide an indication of airway collapse, potentially reducing the need for a nasal cannula to determine patient airflow. In a further example embodiment, the throat cuff may be designed to electrically stimulate the throat and/or neck muscles, for example, by providing a small short pulse when airway collapse is detected and/or when snoring is detected.

2. Example System Components

2.1 Example Power Mechanisms, Sensors, and Data Recorders

Figure 3D:
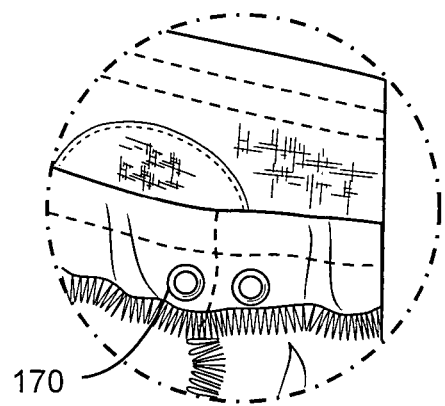

At least a portion of the bed clothing may be formed of fiber battery textiles. Certain electronic textiles are disclosed in Service, Robert F. "Electronic Textiles Charge Ahead," *Science* 301 (Aug. 15, 2003): 909-11. The battery fibers may be charged up, for example, via an operable connection to the main power supply prior to use, and the battery fibers may store the power for later use. Alternatively, or in addition, the pants 114 may be connected to the shirt 112 via a power connection 170 (see FIG. 3d). In one embodiment the shirt 112 may be used separately from the pants and thus may require a connection to a battery at the power connection 170. In certain example embodiments, this power connection may not be required when devices are separated if the shirt 112 has similar battery fibers located therein to hold a charge in the manner described above in relation to pants 114. The fibers woven into the bed clothing may be configured to optionally provide a heating system to increase comfort while wearing the bed clothing.

Figure 4:
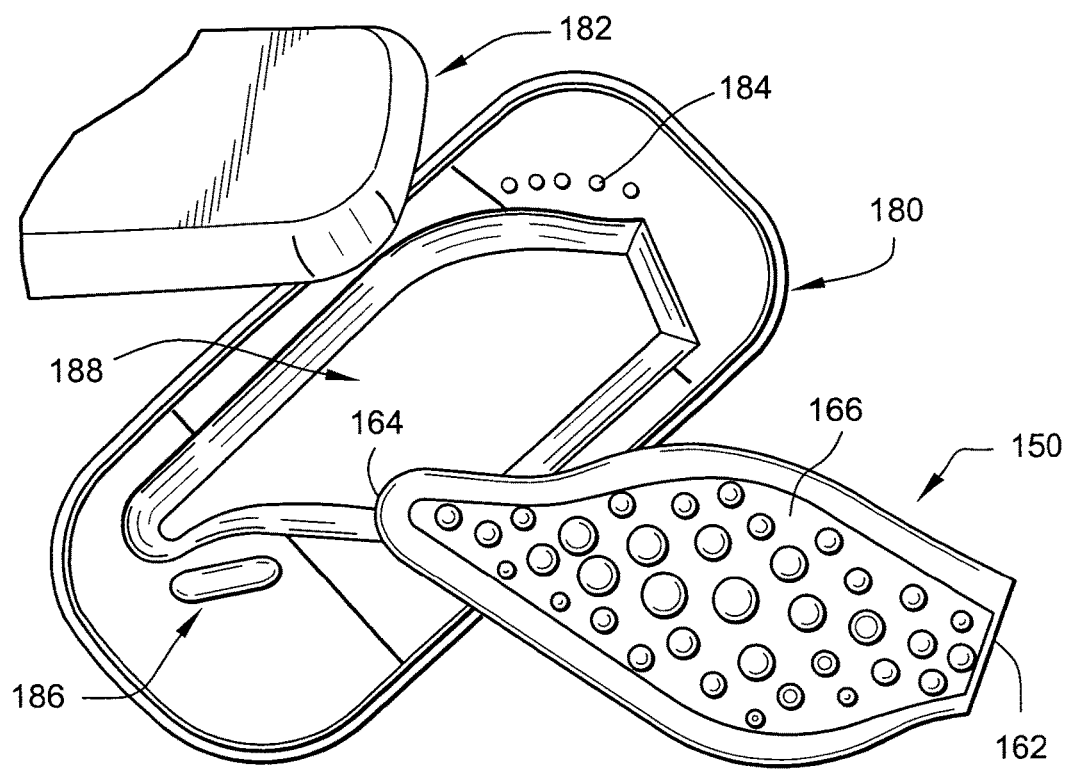
FIG. 4 is a data recorder and data storage case according to an example embodiment.

According to certain example embodiments, a data storage device may be located on the bedside table, and the sensors in the bed clothing may send the data to the unit wirelessly. In certain other example embodiments, a data recorder 150 may be removably located on the patient, and it may be in operable communication (e.g. wireless communication and/or in physical connection with circuitry located within the bed clothing, etc.) with the sensors. Accordingly, FIG. 4 shows an example data recorder 150 together with the data storage case 180 and lid 182. The data recorder may be made from plastic or polycarbonate material, for example. The underside of the data recorder 150 comprises a soft molded surface 166, shown having a number of raised mounds (described in further detail below). Data recorder 150 may comprise a PCB and memory chip, and it may have a wireless communicator to facilitate communication between the data recorder 150 and the data storage case 180.

The data recorder 150 may be stored in the data storage case 180, and the lid 182 may be placed on top. The data storage case 180 has a recorder receiving portion 188 that is molded or shaped to receive the data recorder 150. Various readouts are provided on the display. By way of example and without limitation, light emitting diodes (LED) 184 on the data storage case 180 indicate the connection of different sensor components and the level of charge of the battery. The diagnostic bed clothing apparatus may be operated using a start/stop button 186 present on the data storage case 180.

Figure 5:
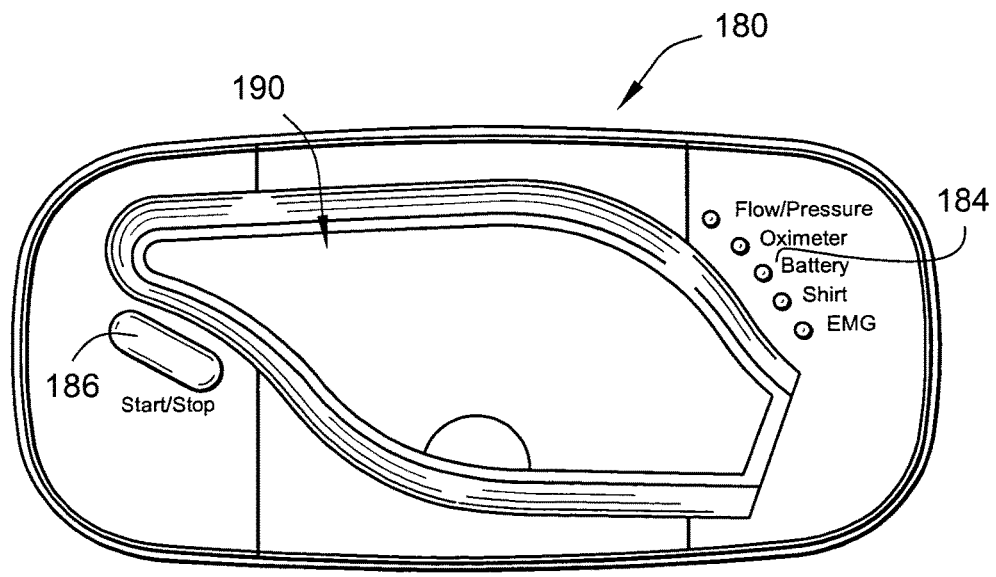
FIG. 5 is a top view of the storage case with the lid removed according to an example embodiment.

FIG. 5 shows a top view of the data storage case 180 indicating an optional internal flap 190 that flips up to allow access to a battery charging unit. A battery may be connected to or inserted into the data storage case 180 and charged for later use. In particular, in certain example embodiments, data storage case 180 may serve as an induction charger to charge a battery included in data recorder 150. The data storage case 180 comprises an electrical plug connection (not shown) to allow the case to be plugged into the main power supply.

Figure 6A:
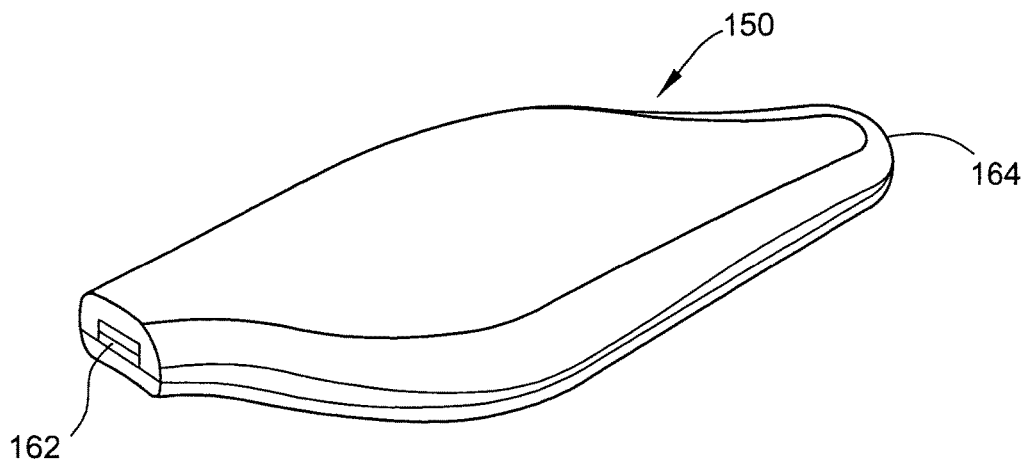
FIG. 6a is a perspective view of the data recorder shown in FIG. 4.
Figure 6B:
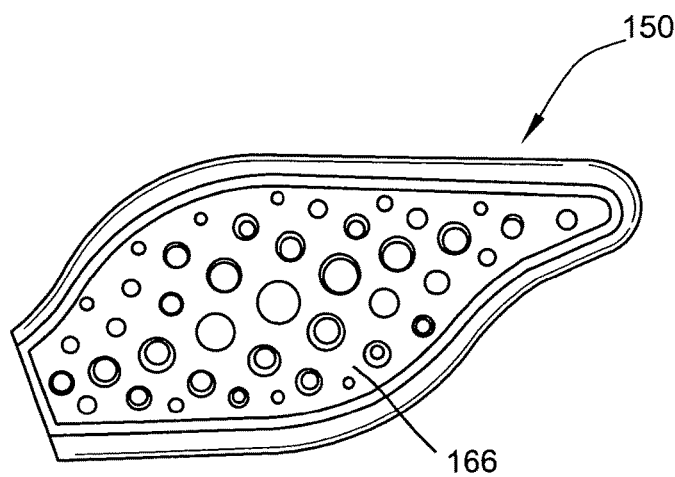
FIG. 6b is a bottom view of the data recorder shown in FIG. 4, showing a molded surface.
Figure 6C:
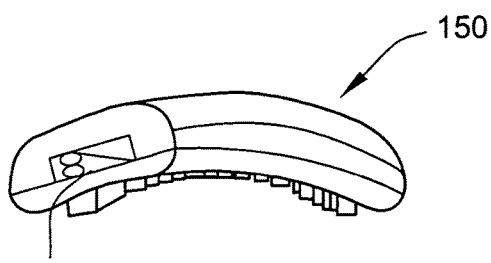
FIGS. 6c and 6d are front and back views of the data recorder of FIG. 4, respectively.
Figure 6D:
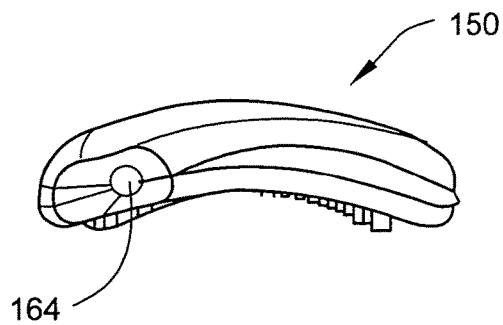
Figure 7A:
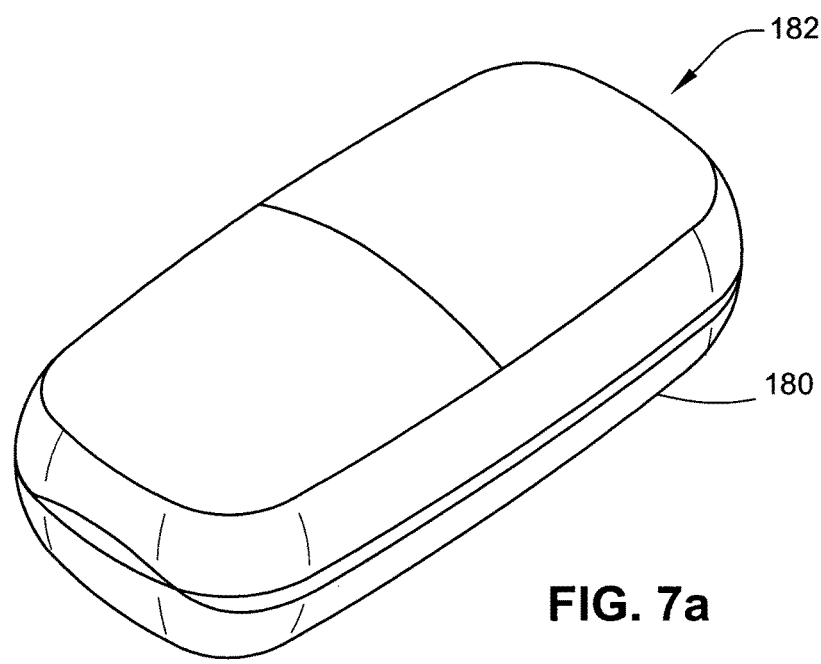
FIG. 7a is an isometric view of the data storage case shown in FIG. 4 with the lid attached.
Figure 7B:
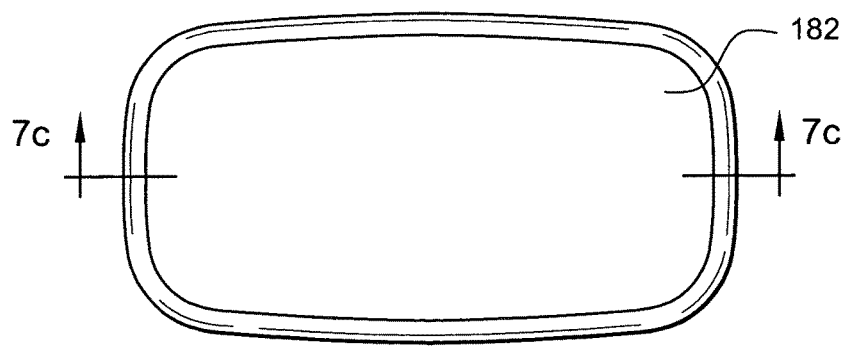
Figure 7C:
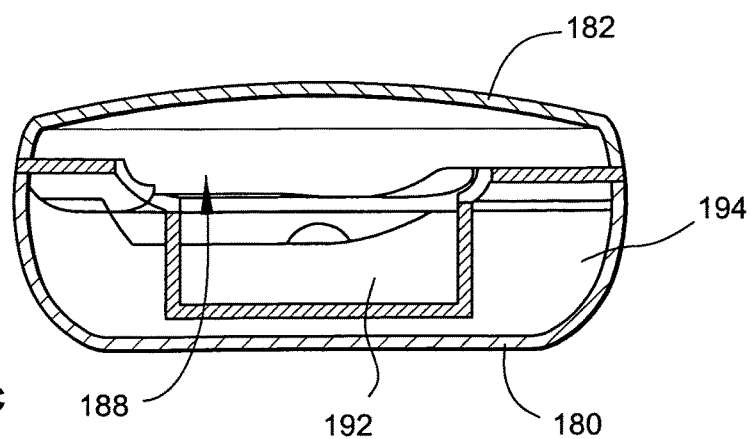
FIG. 7c is a sectional view through 7c-7c of FIG. 7b.
Figure 7D:
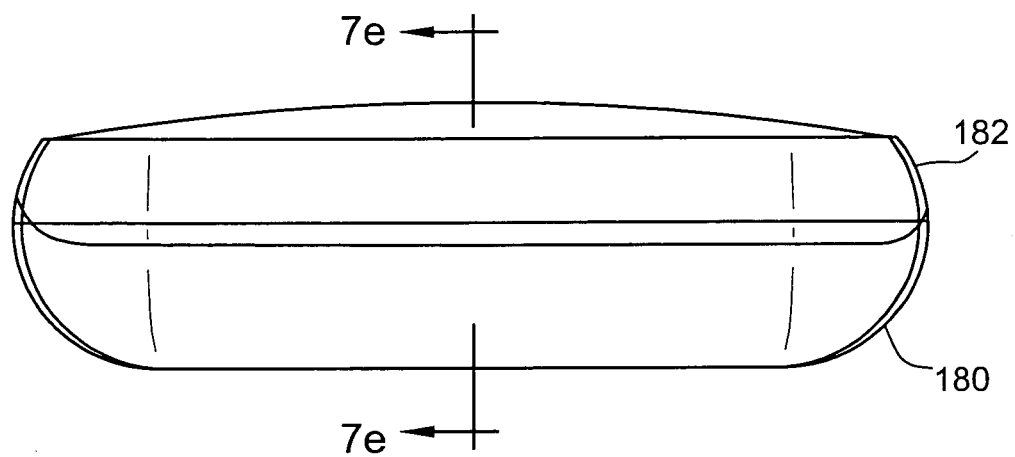
Figure 7E:
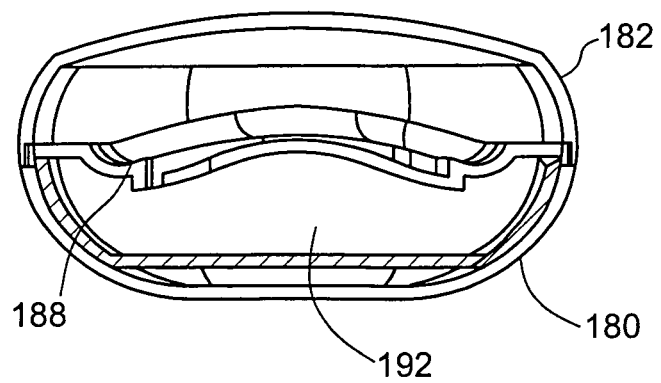
FIG. 7e is a sectional view through 7e-7e of FIG. 7d.

FIGS. 6a and 6b show respectively prospective and bottom views of the data recorder 150. The data recorder 150 is shown as a teardrop-like shaped device with a generally concave profile, as perhaps best seen in FIGS. 6c and 6d. The first connection port 162 is located at the front of the recorder (see FIG. 6c) and the optional second connection port 164 is located at the back of the recorder (see FIG. 6d).

FIGS. 7a to 7e show the data storage case 180 with the lid 182 attached. The data storage case 180 is connected to the main power supply (not shown) and uses wireless technology to communicate with the data recorder 150. Wireless technology, such as Bluetooth, may also be used to download stored data to a computer for analysis. The data storage unit 180 may also comprise a compartment for connecting and charging a battery 192. The PCB is located in the lower portion 194 of the data storage case 180.

FIGS. 8a to 8e show the soft molded surface 166 that is in contact with the receiving portion 188 of the data storage case 180 in greater detail. As noted above, surface 166 has a number of raised mounds, and these raised mounds allow air to flow around the device when in use. Molded surface 166 is designed to be positioned closest to the patient's body, and molded surface is designed to provide increased comfort for the patient and to allow airflow between the patients' body and data recorder 150. The soft molded surface is attached to the bottom surface of the data recorder using any suitable fastener including, for example, adhesives, small screws, etc. It will be appreciated that any surface that enhances the comfort of the patient may be used instead of or in addition to the raised mounds. For example, the molded surface may be manufactured from the same material as the data recorder 150, and the molded surface may be produced during manufacture. The casing itself may provide enough comfort, thus removing the need for additional mechanical features. In an alternative example embodiment, the data recorder 150 may be made from or encased in a soft pliable material such as a gel-like material that allows data recorder 150 to comfortably form to a patient's arm.

2.2 Locating Data Recorders and/or Batteries on the Patient

In the case where a data recorder is present on the person (e.g. in systems where wireless communications are not implemented, etc.), the bed clothing system may be configured to receive the data recorder unit in a number of different locations, such as, for example, the chest, back, arm, ankle, etc. The location of the data recorder unit may be selected depending on the sleeping pattern and positions of the individual patient to be tested. A battery pack may be disposed in a similar fashion when chargeable fibers are not located in the bed clothing articles. As noted above, pockets may be formed in the bed clothing to accommodate the data recorder and/or battery.

In addition to the molded portions on the data recorder, the battery pack and/or the data recorder may be shaped and contoured to fit the body profile. Even with a battery located on the patient, the shape and location thereof may be selected to allow patient movement and increased comfort. For example, the battery pack may be designed to be longer but thinner, spreading the load to provide increased comfort (e.g. it may attach across the back and/or front of the shirt).

Alternatively or in addition, the control buttons may be present on a watch-like (or band) device, configured to be placed on the patient's wrist, ankle, etc. Thus, the patient may easily control settings during the night if required. For example, the patient may turn the system off if they get up during the night and then restart it again once they return to bed. Data recorders may be located in or operably connected to such watches.

3. Outfitting a Patient with Example Bed Clothing 3.1 Wearing Example Bed Clothing In an example embodiment, the diagnostic bed clothing is used to perform a sleep disorder diagnosis on a patient. The diagnostic bed clothing is worn by the patient. The data recorder 150 is inserted into the pocket on the bed clothing and attached to the data connector 154 via the first connection port 162. An oximeter is attached to the finger of the patient, and the associated wiring is operably connected to the optional second connection port 164 of the data recorder. A nasal cannula may be placed in the patients nostrils to record the airflow, also operably connected via the optional second connection port 164. This tubing is operably connected to the data recorder via the data connector 154. Optionally, prior to use the location and activation of the sensors may be monitored to ensure satisfactory readings can be received.

The diagnostic bed clothing apparatus may be used with the shirt 12, 112, and alone or together with the pants 14, 114. When the pants 14, 114 are used, the power connection 28, 170 between the shirt 12, 112 and the pants 14, 114 is operably connected. Alternatively the shirt 12, 112 may be connected directly to a battery at the power connection 28, 170 or any other suitable location on the shirt. In certain example embodiments, the data recorder may also comprise the battery to provide power for the sensors.

3.2 Collecting Data via the Sensors

Once the patient is ready for sleep, the patient presses the start/stop button 186 to activate the diagnostic system (or a similar button on a watch if such a mechanism is provided). A number of events may occur to initialize the apparatus. First, the LEDs 184 on the case may light up to indicate that the connections are all functioning. Second, the case may emit signals to the data recorder (e.g. via a wireless technology, such as, Bluetooth, or any other wireless technology). The emitted signals may activate the sensors and initiate the recording of data. The sensor activation may activate the artificial muscle contraction fibers to contract the bed clothing firmly against the patient's body, thus ensuring satisfactory connections for the sensors.

While the patient is sleeping, the diagnostic bed clothing may record information relating to sleep parameters that will assist in diagnosing a range of sleep disorders. The information recorded by the sensors 134 is sent to the data storage case 180 (e.g. via wireless technology, such as, for example, Bluetooth). The data storage case 180 may facilitate the transfer (e.g. download) of sleep data from data recorder 150 to a computer or the like for analysis. For example, the data storage case 180 may include a memory device of its own to at least temporarily receive and store data, or it may merely serve as an intermediary for data exchange between data recorder 150 and a suitably configured peripheral device (e.g. by providing connection interfaces, such as, for example FireWire. USB, serial or parallel communicates, etc.). Upon waking in the morning, the patient may simply press the start/stop button to turn the sensors off and stop the recording. In case a patient wakes in the night, the apparatus may be started and stopped numerous times, and the data maintained in the data storage case may be recorded for each individual session.

Following the completion of the sleep study, the sensor unit may be removed from the diagnostic bed clothing and stored in the data storage case for later use. A plug may be placed over the data connector, and the diagnostic bed clothing may be laundered without affecting the data recorder. Alternatively, or in addition, the bed clothing system may be disposable with removable and reusable data logic and/or battery devices. The system may also have removable and reusable sensors, thus reducing the costs associated with the bed clothing system.

4. Example Bed Sheet Embodiments

4.1 Bed Sheets Functioning as Diagnostic Bed Clothing

Figure 9B:
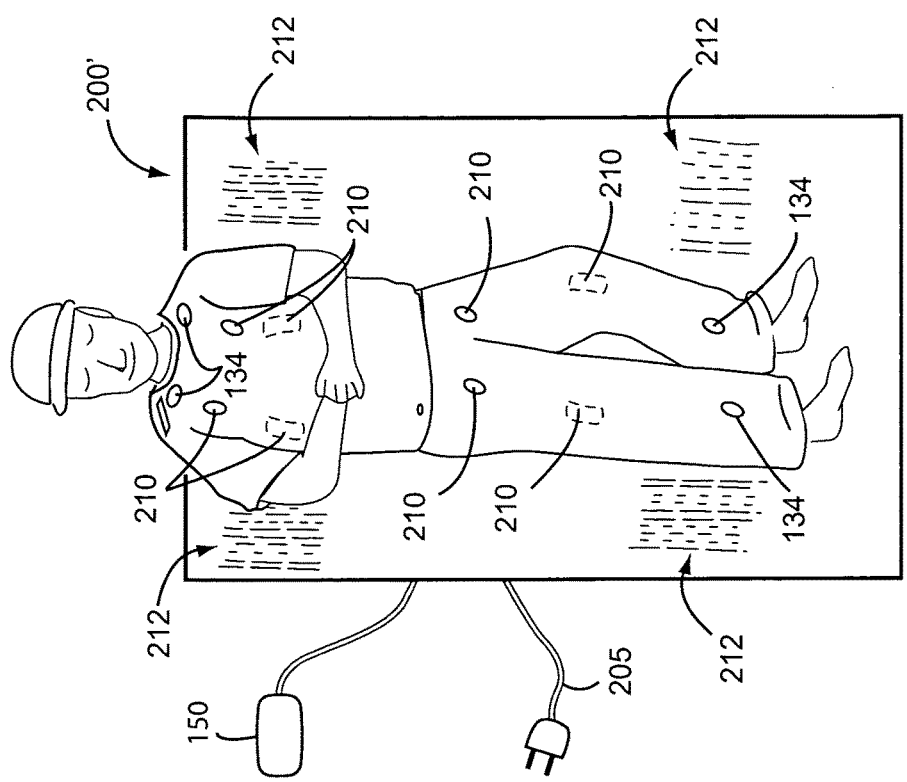
FIG. 9b is an example diagnostic bed sheet for use with diagnostic bed clothing, in accordance with an example embodiment; and, FIG. 9c is an example diagnostic bed sheet for use with diagnostic bed clothing and a flow generator in accordance with an example embodiment.
Figure 9A:
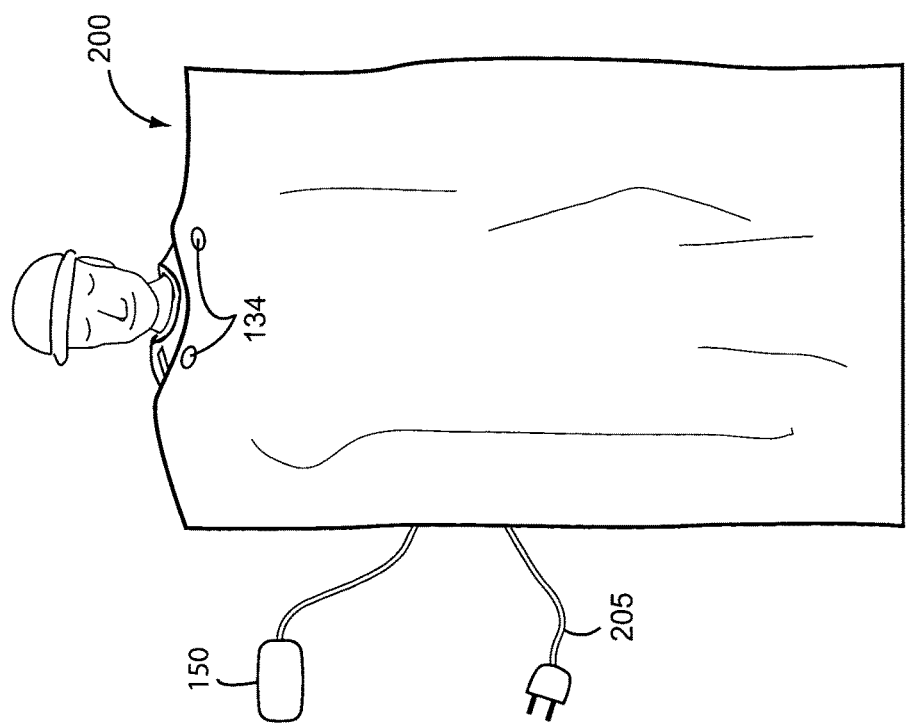
FIG. 9a is an example diagnostic bed sheet apparatus in accordance with an example embodiment.

An alternative to using the wearable bed clothing described above includes using a bed sheet similar to an electric blanket, as shown, for example in FIG. 9b, which is an example diagnostic bed sheet apparatus in accordance with an example embodiment. Such a bed sheet may be operable to measure a sleeping person's biorhythms, similar to sensing blankets used in neonatal intensive care units. However, it will be appreciated that although such sensing blankets used in neonatal intensive care units may measure a baby's heart rate, movement, temperature, etc. and may include oximeters, EEG and/or ECG electrodes, such techniques are unknown in the field of diagnosing OSA. The sensors may simply sound alarms. In certain example embodiments, sensors 134 similar to those described above may be disposed in the bed sheet 200, and similar batteries may be used. Bed sheet 200 may be operably connected (e.g. wirelessly connected) to data recorder 150 and/or data storage case 180. Bed sheet 200 also may be connected to a power source via power connection 205. Thus, in certain example embodiments, these bed sheets may take the place of all diagnostic bed clothing described above.

In certain other example embodiments, an alternative system may comprise one or more conductive bed sheets (or mats above/below regular sheets or beneath the bed mattress), which may be positioned in the bed under the patient. For example, one bed sheet/mat may be positioned under the patient's lower body and/or legs, and a second sheet may be positioned under the patient's head and/or upper body. Still further, the bed sheet may be placed in or under a pillow, or the sensor(s) could be formed as part of the pillow or pillow case. Alternatively, or in addition, a single bed sheet may have multiple zones defined therein. These zones may operably connect the bed sheet to contacts in wearable bed clothing. Each bed sheet/mat may comprise conductive bands to provide power and logic signals to the system. FIG. 9b shows a plurality of conductive bands 212 disposed throughout the bed sheet. It will be appreciated that conductive bands 212 may run the length of the bed sheet, effectively may divide the bed sheet into zones, may be optimized for contact with certain wearable bed clothing, etc. Thus, it will be appreciated that the location and amount of conductive bands 212 shown in FIG. 9b are provided by way of example and without limitation.

4.2 Bed Sheets Function with Diagnostic Bed Clothing

In certain example embodiments, a bed sheet/mat may be used together with diagnostic bed clothing. In such example embodiments, receivers in the shirt/pants/shorts/cap may pick up the current from the bed sheets/mats to provide power. This may be advantageous, for example, because the bed sheets/mats can be more statically positioned under the patient and be independent of the movement of the patient, which typically causes problems in conventional diagnostic systems. For example, FIG. 9b is an example diagnostic bed sheet 200' for use with diagnostic bed clothing, in accordance with an example embodiment.

Bed sheet 200' may include conductive bands to facilitate the transfer of power and/or data between the wearable shirt/pants/cap and the bed sheet via contacts 210. The contacts 210 may be disposed in a plurality of positions on the clothing. The diagnostic bed clothing may include one or more contacts 210 so that it stays in operable connection with the bed sheet, regardless of the position of the patient. In this way, it may be easier to provide power and/or data transmissions to/from the bed clothing through a more permanent connection between the bed sheet/mat and the power source and/or data recorder 150. It also may be easier to store diagnostic information (e.g. without using a wireless communicator), as the bed sheet/mat may be connected to a recording device directly. Preferably, one contact (or set of contacts) will be located on the patient's upper body area (e.g. shirt), and one contact (or set of contacts) will be located on the patient's lower body and/or leg areas (e.g. pants). Thus, power and/or logic signals may be transmitted through these contacts, and the bed clothing may still function even though the patient moves freely during sleep.

5. Use in Continued Patient Monitoring

In a further example embodiment, the bed clothing system may be used for continued monitoring of a patients condition already being treated (e.g. with CPAP treatment, etc.). Thus, the bed clothing system may be used in combination with the use of a CPAP system. The continued monitoring may be for an initial predetermined period when the patient commences therapy and/or for routine monitoring (e.g. annually or bi-annually), to provide information on the effectiveness of the treatment. This may provide feedback to the patient and the clinician regarding the benefits of the treatment. Also, it may be possible to identify issues regarding whether a sufficient treatment pressure is being provided. The example embodiments accordingly may provide information relating to orientation, movement, heart rate, oxygen saturation, etc. Thus, a nasal cannula may not be required when using the bed clothing system in combination with a CPAP device.

Figure 9C:
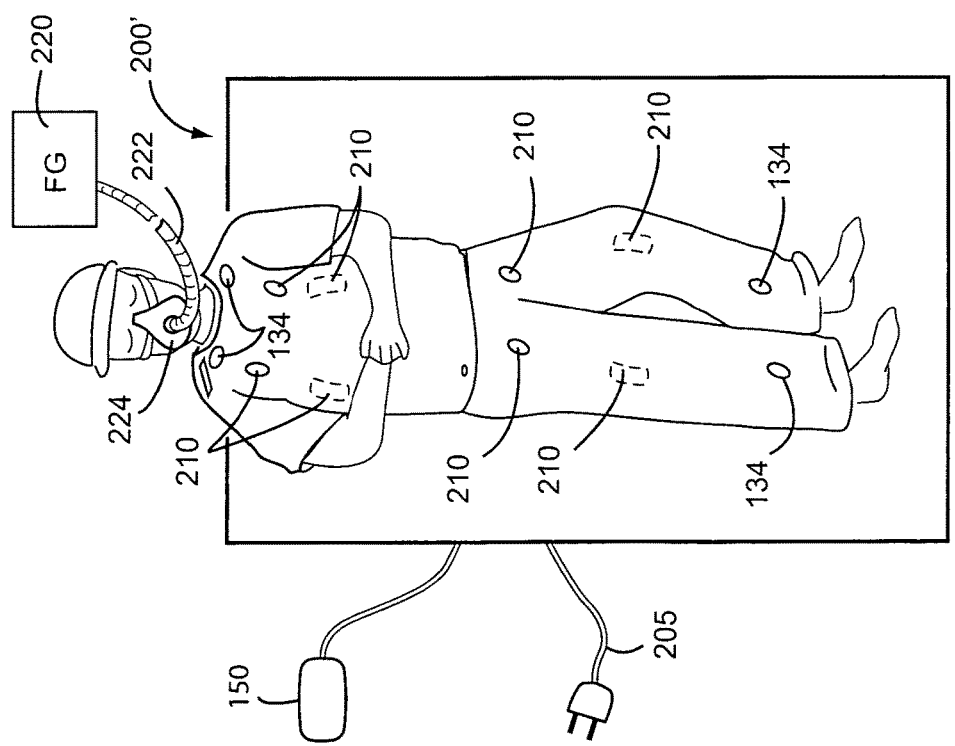

For example, FIG. 9c is an example diagnostic bed sheet for use with diagnostic bed clothing and a flow generator in accordance with an example embodiment. Although described in relation to bed sheet 200', it will be appreciated that a flow generator 220 could be configured for use with various combinations of bed clothing. In FIG. 9c, flow generator 220 delivers a supply of pressurized breathable gas to the patient flexible tube 222, which connects mask 224 to flow generator 220. The bed clothing may monitor the responses to the treatment. Additionally, in certain example embodiments, flow generator 220 may be configured to receive signals generated by the bed clothing. The flow generator 220 thus may alter the parameters of the delivered treatment in response thereto.

6. Anticipated Advantages

Certain example embodiments may comprise fibers that provide sensing signals and power, but may nonetheless feel comfortable and natural to wear. For example, certain example embodiments advantageously may provide a more comfortable and easier to use diagnostic device. For example, freedom from wires may allow for natural body movement during sleep. Without large equipment, the number of pressure points caused by such equipment may be reduced and/or completely eliminated. Thus, the patient may be able to enjoy a normal night's rest. Furthermore, the patient may not feel self-conscious while wearing the garment.

The diagnostic bed clothing also may provide advantages to physicians, for example, in that there is no need to set a recording time. There also may be less chance for error when the patient sets up the system. With the patient being more comfortable, it is believed that a more accurate indication of the patients condition may be obtained. Consequently, the physician may be able to make a more accurate diagnosis. If headgear is included, the physician may obtain an even better indication of the severity of the patient's condition and also obtain a better indication of the condition that the patient suffers from, as many sleep disorders present the same symptoms. Thus, the diagnostic bed clothing may be used to diagnose a range of sleep disorders. A further benefit of the example embodiments is that there is less chance for damage or loss of components, as they are all contained within the pajamas or bed clothes.

It will be appreciated that while the example embodiments herein have sometimes been described with certain combinations of articles of bed clothing, the invention is not so limited. For example, shirts and pants may be used together or apart, depending on the particular example embodiment implemented. As a further example, either, both, or neither may be combined with headgear, depending on the particular example embodiment implemented.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments.

Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in nonmedical applications.

What is claimed is:

1. A diagnostic system for use in diagnosing a patient with a sleep disorder, comprising:
   at least one item of bed clothing, the at least one item of bed clothing comprising at least one sensor; and
   a data recorder in operable communication with the at least one sensor;
   wherein the at least one sensor is operable to monitor at least one sleeping disorder related parameter and further operable to communicate the at least one sleeping disorder related parameter to the data recorder,
   wherein the data recorder is shaped and/or contoured to fit the patient's body, the data recorder having a patient-facing surface adapted to be placed closest to and in indirect contact with the patient, the patient-facing surface including a plurality of projections that protrude therefrom and that are adapted to facilitate airflow between the patient's body and the data recorder when the data recorder is being worn by the patient and is in use.

2. The system of claim 1, wherein the at least one item of bed clothing further comprises artificial muscle fibers, the artificial muscle fibers being configured to cause the item of bed clothing to contract.

3. The system of claim 1, wherein the at least one item of bed clothing further comprises a cinching mechanism configured to cause the item of bed clothing to contract.

4. The system of claim 1, further comprising a power source operable to supply power to the at least one sensor.

5. The system of claim 4, further comprising a battery mechanism operably connected to the power source, the battery mechanism being configured to warm the patient via heat generated by the battery mechanism.

6. The system of claim 4, further comprising a battery mechanism operably connected to the power source, the battery mechanism comprising fibers woven into the item of bed clothing.

7. The system of claim 1, wherein the at least one sleeping disorder related parameter includes one or more of: patient orientation, patient movement, heart rate, oxygen saturation level, snore, an apnea and/or hypopnea event, respiratory effort, oximetry, and/or neck muscle tone.

8. The system of claim 1, further comprising a pocket formed in the at least one item of bed clothing for receiving the data recorder and/or a battery.

9. The system of claim 8, wherein the at least one item of bed clothing is a shirt, and the pocket is formed on a shoulder, arm, chest, and/or back of the shirt.

10. The system of claim 1, further comprising a battery, the battery being rechargeable.

11. The system of claim 10, further comprising a data storage case for receiving the data recorder, the data storage case being operable to recharge the battery.

12. The system of claim 1, wherein the at least one item of bed clothing is headgear.

13. The system of claim 12, wherein the at least one sensor comprises an EEG sensor.

14. The system of claim 12, wherein the at least one sensor comprises an oximeter configured for connection to an earlobe of the patient.

15. The system of claim 1, wherein the at least one item of bed clothing is a glove comprising an oximeter connected to a finger of the patient.

16. The system of claim 1, wherein the at least one item of bed clothing is a throat cuff.

17. The system of claim 16, wherein the at least one sensor is a vibration sensor operable to detect patient snore.

18. The system of claim 16, wherein the throat cuff is operable to measure a muscle tone of the patient's neck and/or operable to electrically stimulate the patient's throat and/or neck muscles in response to a collapse of the patient's airway and/or patient snore.

19. The system of claim 1, wherein the at least one item of bed clothing comprises two or more articles of bed clothing.

20. The system of claim 19, further comprising an exchange mechanism operable to allow power and/or data to flow between the two or more articles of bed clothing.

21. The system of claim 19, wherein the two or more articles of bed clothing comprises a shirt and pants.

22. The system of claim 19, wherein a second item of bed clothing is configured to communicate at least one sleeping disorder related parameter from the at least one sensor in the second item of bed clothing to the data recorder via a bed sheet or mat positioned above and/or below a mattress.

23. The system of claim 1, wherein the data recorder is located remote from the at least one item of bed clothing.

24. The system of claim 1, wherein the at least one item of bed clothing is pants, and a pouch for accommodating the data recorder is formed at an ankle of the pants.

25. The system of claim 1, further comprising a watch operable to cause the diagnostic system to start and/or stop monitoring data.

26. The system of claim 1, further comprising a flow generator operable to provide a supply of pressurized breathable gas to the patient.

27. The system of claim 26, wherein the flow generator is further operable to adjust the supply of pressurized breathable gas in response to one or more signals generated by the at least one sensor.

28. The system of claim 1, wherein the patient-facing surface and other outer surfaces of the data recorder are formed from the same material.

29. The system of claim 1, wherein the patient-facing surface is a soft-molded surface formed from the same material as the data recorder.

30. The system of claim 1, wherein the patient-facing surface is attached to the data recorder via at least one fastener.

31. A diagnostic system for use in diagnosing a patient with a sleep disorder, comprising:
- at least one item of bed clothing, the at least one item of bed clothing comprising at least one sensor; and
- a data recorder in operable communication with the at least one sensor;
- wherein the at least one sensor is operable to monitor at least one sleeping disorder related parameter and further operable to communicate the at least one sleeping disorder related parameter to the data recorder,
- wherein the at least one item of bed clothing further comprises electronically controllable artificial muscle fibers, the artificial muscle fibers being configured to cause the item of bed clothing to contract to more closely fit the patient, and
- wherein the at least one sensor and the data recorder are operable to communicate via a wireless connection.

32. A diagnostic system for use in diagnosing a patient with a sleep disorder, comprising:
- two or more articles of bed clothing, the two or more articles of bed clothing comprising at least one sensor;
- a data recorder in operable communication with the at least one sensor; and
- an exchange mechanism operable to allow power and/or data to flow between the two or more articles of bed clothing,
- wherein the at least one sensor is operable to monitor at least one sleeping disorder related parameter and further operable to communicate the at least one sleeping disorder related parameter to the data recorder, and
- wherein the exchange mechanism comprises a fastener engagably and cablelessly connecting the two or more articles of bed clothing.

33. A diagnostic system for use in diagnosing a patient with a sleep disorder, comprising:
- at least one item of bed clothing, the at least one item of bed clothing comprising at least one sensor; and
- a data recorder in operable communication with the at least one sensor;
- wherein the at least one sensor is operable to monitor at least one sleeping disorder related parameter and further operable to communicate the at least one sleeping disorder related parameter to the data recorder,
- wherein the at least one item of bed clothing is a bed sheet or mat positioned above and/or below a mattress, and
- wherein the bed sheet or mat is configured to supply power to the at least one sensor included in a second item of bed clothing to be worn by the patient via at least one contact between the bed sheet or mat and the second item of bed clothing.

34. The system of claim 33, wherein the second item of bed clothing comprises a plurality of contacts disposed on a plurality of sides of the second item of bed clothing.

35. The system of claim 33, further comprising an operable connection between the bed sheet or mat and a power source and/or the data recorder, the operable connection being a physical connection.

36. The system of claim 33, further comprising an operable connection between the bed sheet or mat and the data recorder, the operable connection being a wireless connection.

37. A method for diagnosing a patient with a sleep disorder, the method comprising:
- providing at least one item of bed clothing to the patient, the at least one item of bed clothing comprising at least one sensor;
- generating a signal corresponding to at least one sleeping disorder related parameter of the patient via the at least one sensor; and,
- recording the signal onto a data recorder via a data recorder, the data recorder being shaped and contoured to fit the patient's body, the data recorder being formed from or encased in a soft, pliable material structured to enable the data recorder to comfortably form to the patient's body in a non-contacting manner.

38. The method of claim 37, further comprising:
providing at least two items of bed clothing; and
exchanging the signal and/or power between the at least two items of bed clothing.

39. The method of claim 37, further comprising placing the at least one item of bed clothing under the patient, the at least one item of bed clothing being a bed sheet.

40. The method of claim 37, further comprising providing a supply of pressurized breathable gas to the patient.

41. The method of claim 40, further comprising adjusting the supply of breathable gas in response to the signal.

42. A method for diagnosing a patient with a sleep disorder, the method comprising:
- providing at least one item of bed clothing to the patient, the at least one item of bed clothing comprising at least one sensor;
- generating a signal corresponding to at least one sleeping disorder related parameter of the patient via the at least one sensor;
- recording the signal onto a data recorder via a data recorder, the data recorder being shaped and contoured to fit the patient's body; and,
- causing the at least one item of bed clothing to contract to correspondingly cause the at least one item of bed clothing to more closely fit the patient using electronically controllable muscle fibers embedded in the at least one item of bed clothing.

43. A system for diagnosing a patient with a sleep disorder, comprising:
- at least one item of bed clothing for the patient, the at least one item of bed clothing comprising at least one sensor;
- means for generating a signal corresponding to at least one sleeping disorder related parameter of the patient; and,
- means for recording the signal onto a data recorder,
- wherein the data recorder is shaped and contoured to fit the patient's body, and
- wherein the at least one item of bed clothing further comprises electronically controllable artificial muscle fibers, the artificial muscle fibers being configured to cause the item of bed clothing to contract during a diagnostic session.

* * * * *